(12) United States Patent
Shchukin et al.

(10) Patent No.: US 10,874,530 B2
(45) Date of Patent: Dec. 29, 2020

(54) METHOD OF BIONIC CONTROL OF TECHNICAL DEVICES

(71) Applicants: Sergey Igorevich Shchukin, Moscow (RU); Aleksandr Viktorovich Kobelev, Kursk Region (RU); Igor Konstantinovich Sergeev, Ramenskoye (RU); Oleg Stepanovich Naraykin, Moscow (RU)

(72) Inventors: Sergey Igorevich Shchukin, Moscow (RU); Aleksandr Viktorovich Kobelev, Kursk Region (RU); Igor Konstantinovich Sergeev, Ramenskoye (RU); Oleg Stepanovich Naraykin, Moscow (RU)

( * ) Notice: Subject to any disclaimer, the term of this patent is extended or adjusted under 35 U.S.C. 154(b) by 116 days.

(21) Appl. No.: 16/085,529

(22) PCT Filed: Mar. 6, 2017

(86) PCT No.: PCT/RU2017/000114
§ 371 (c)(1),
(2) Date: Sep. 14, 2018

(87) PCT Pub. No.: WO2017/160183
PCT Pub. Date: Sep. 21, 2017

(65) Prior Publication Data
US 2019/0099279 A1    Apr. 4, 2019

(30) Foreign Application Priority Data
Mar. 15, 2016  (RU) ................. 2016109214

(51) Int. Cl.
*A61F 2/72*   (2006.01)
*A61F 2/48*   (2006.01)
(Continued)

(52) U.S. Cl.
CPC ............ *A61F 2/72* (2013.01); *A61B 5/04001* (2013.01); *A61B 5/04012* (2013.01);
(Continued)

(58) Field of Classification Search
CPC ........................................ A61F 2/72
See application file for complete search history.

(56) References Cited

U.S. PATENT DOCUMENTS

| | | | | |
|---|---|---|---|---|
| 3,735,425 A | * | 5/1973 | Hoshall | A61B 5/0428 623/25 |
| 5,888,213 A | * | 3/1999 | Sears | A61F 2/68 623/24 |
| 2007/0038311 A1 | * | 2/2007 | Kuiken | A61F 2/68 623/24 |

(Continued)

FOREIGN PATENT DOCUMENTS

EP    2 687 898 A1    1/2014

OTHER PUBLICATIONS

Lewis, S. et al. 2013 "Fully implantable multi-channel measurement system for acquisition of muscle activity" *IEEE Transactions on Instrumentation and Measurement* 62: 1972-1981.

(Continued)

*Primary Examiner* — Jacqueline Woznicki
(74) *Attorney, Agent, or Firm* — Knobbe, Martens, Olson & Bear, LLP

(57) ABSTRACT

Methods of bionic control of a device include passing an alternating current through a muscle to cause the muscle to contract, recording an electrophysiological signal from the contracting muscle, processing the electrophysiological signal to determine a measurement of electrical impedance, forwarding the measurement of electrical impedance to a controller, and controlling the device with a control action. A change of electrical impedance during muscle contraction is used as a basis for the control action.

17 Claims, 4 Drawing Sheets

(51) Int. Cl.
    *A61B 5/04*     (2006.01)
    *A61B 5/053*     (2006.01)
    *A63F 13/212*     (2014.01)
    *A61B 5/0488*     (2006.01)
    *A61B 5/0492*     (2006.01)
    *A61B 5/00*     (2006.01)
    *A61F 2/02*     (2006.01)
    *G06F 3/01*     (2006.01)

(52) U.S. Cl.
    CPC .......... *A61B 5/0488* (2013.01); *A61B 5/0492* (2013.01); *A61B 5/04888* (2013.01); *A61B 5/053* (2013.01); *A61B 5/4851* (2013.01); *A61F 2/02* (2013.01); *A63F 13/212* (2014.09); *G06F 3/015* (2013.01); *A61B 5/0531* (2013.01); *A61B 5/0538* (2013.01); *A61F 2002/482* (2013.01)

(56) References Cited

U.S. PATENT DOCUMENTS

| 2012/0116741 | A1 | 5/2012 | Choi et al. | |
| 2015/0142129 | A1* | 5/2015 | Kim | A61F 2/72 623/25 |
| 2015/0173918 | A1* | 6/2015 | Herr | A61F 2/68 623/25 |
| 2018/0028390 | A1* | 2/2018 | Dietl | A61F 2/64 |
| 2019/0099279 | A1* | 4/2019 | Shchukin | A63F 13/212 |

OTHER PUBLICATIONS

Nahrstaedt, et al. 2010 "Bioimpedance based measurement system for a controlled swallowing neuro-prosthesis" *Proc. of 15th Annual International FES Society Conference and 10th Vienna Int. Workshop on FES*, pp. 49-51.

* cited by examiner

METHOD OF BIONIC CONTROL OF TECHNICAL DEVICES

FIELD

The present invention relates to biophysics and medical technology, and it can be used for controlling special technical devices, for example, bioelectric prostheses, electronic implants, or exoskeletons, by means of a computer, game console or another special technical device.

BACKGROUND

The principle of operation of bioelectric prostheses is based on the fact that after amputation, there is some muscle tissue remaining on the stump that is capable of contracting. It results in the occurrence of electric potential in the muscle, which is recorded and transmitted to the microprocessor of the prosthesis.

An exoskeleton is a device intended to restore the lost functions, increase muscular strength and expand movement amplitude of a person by means of an external frame and driving elements.

A robotic device is a device including robots, robot effectors (operating tools) and machines, equipment, devices and sensors supporting robots during operation.

Electroneurography is a method of researching the velocity of electric impulse conduction through the nerves.

An electromyogram signal is a signal received as a result of a muscle contraction occurring as a consequence of a movement intention of a person; it characterizes the bioelectric activity of the muscles.

The development of neurobiology, neurosurgery, microelectronics and digital signal processing technology makes it possible to realize in practice neuro-controlled systems of biotechnical device control.

In recent years, the use of various robotic devices in the sphere of medicine has been on the rise. This trend is related to the development of a corresponding hardware component base of mechatronic and sensory devices, biologically safe materials, as well as methods of obtaining information on the status of individual human body organs.

In developing bio- or neuro-controlled biotechnical devices, it is necessary, first of all, to identify the method of obtaining information on the movement performed.

In modern biotechnical systems, such as, for example, human-computer interaction (HCI) systems, biopotentials are used: electroencephalograms (EEG), electromyograms (EMG), electroneurograms (ENG), electrooculograms (EOG).

Electromyograms have seen the widest use of all.

Myography is recording of the contractile muscle activity. The simplest method of diagrammatic recording of a muscle contraction is mechanical recording with the help of a lever whose free end draws a respective curve, a myogram, on the paper band of a myograph. Besides such mechanical myographs there are optical ones that record the muscle operation on a light-sensitive film or paper. Myographs of different designs ensure the recording of isotonic or isometric muscle contractions. The most accomplished method is one measuring the muscle tension fluctuations with the help of sensors transforming mechanical changes into electric ones that can be recorded and displayed on an oscillograph. That method allows the recording of contractions of individual muscle cells. The method of myography, combined with a number of other physiological methods, makes it possible to study principal patterns of the contractile muscle function.

Electromyography is a research method for studying bioelectric potentials occurring in the skeletal muscles of a human or an animal in cases where muscle fibers are being excited; the recording of electrical activity of muscle fibers.

Electromyography is used for electrophysiological diagnostics of neuromuscular system afflictions.

There is spontaneous electromyogram that reflects the state of the muscles at rest or under stress (spontaneous or synergetic), and induced electromyogram caused by an electrical stimulation of a muscle or a nerve. Electromyography allows conducting topical diagnostics of the damaged nervous and muscular systems (suprasegmental pyramidal and extrapyramidal structures, motor neurons of the frontal horns, spinal roots and nerves, neuromuscular synapse and the innervated muscle itself), evaluating the severity, stage and state of the disease, and the efficacy of the therapy applied.

It is known that a contraction of a muscle is initiated by electrical impulses in the nerve trunks passing to the muscle fibers. These impulses depolarize the muscle cell membranes, resulting in an action potential in the muscle fibers that quickly spreads along the nerve fiber and results in the contraction thereof. Notably, a contraction is only initiated by this action potential, while the contraction process itself is much more protracted. By using needle (invasive) or surface electrodes, it is possible to record the sum of action potentials of all the cells involved in the process. This signal is called the electromyogram signal (EMG) [De Luca, Carlo (2006). Electromyography. Encyclopedia of Medical Devices and Instrumentation, Second Edition, Volume 3. John Wiley Publisher, pp. 98-109]. Subsequent processing thereof and the extraction of informative features of the EMG makes it possible to realize control of technical devices, for example, bioelectrical prostheses. [Alter, Ralph (1966), Bioelectric Control of Prostheses, Technical Report: Massachusetts Institute of Technology, Research Laboratory of Electronics].

The creation of such devices is particularly promising for the purpose of restoring movement capacity after amputations and paralyses, in cases where the residual bioelectrical activity of truncated or paralyzed muscles is used in a natural way to control movements of a prosthesis or an orthopedic device.

In that case, surface or implanted electrodes of the stump generate, as a result of the electrical activity of the muscle, electrical signals that are passed to the amplifier and make it possible to obtain data on the type of the movement performed. These data are transformed into respective control signals of the artificial extremity executive mechanisms. Evidently, to create high-quality prostheses with bio- and neuroelectric control will require a high-quality and stable signal.

The prior art comprises known methods of electromyographic prosthesis control (RU #2108768, 1995; DE #2354885, 1972; RU #2508078, 2010; U.S. Pat. No. 5,888, 213, 1999; FR #2957245, 2011).

A drawback of all known methods of electromyographic prosthesis control is the fact that depolarization signals from the muscles stimulated concurrently overlap, so it is extremely difficult to obtain the EMG signal on the activity of one specific muscle. Besides, the influence of crosswise (interference) distortions from adjoining muscles grows the more is the distance between the measuring electrodes.

At the same time, EMG signals reflect the beginning of the muscle contraction well, but do not give a true idea of the nature of the muscle movement during contraction.

Besides, although the EMG signal is one of the simplest electrophysiological signals for measurement, it is one of the most difficult for quantitative interpretation. Therefore, to identify various movements with the help of EMG signals, more electrode systems need to be placed on the muscle, which is not always practicable, for example, when the scope of amputation is substantial.

There are known methods of determining contractile muscle capacity, which is recorded at neuromuscular function control (degree of neuromuscular block) during general anesthesia. The methodology of assessment is based on the use of diagnostic electroneurostimulation (Gecht, Kolomenskaya, Strokov, 1974; Voronovich, Shalatonina, 1979; Starobinets, Volkova 1981; Molla-Zadeh, Zenkov, 1984). For that purpose, skeletal muscles are subjected to excitation with electric current impulses. The intensity of muscular response to an external stimulation reflects the state of neuromuscular transmission and, correspondingly, the influence of myorelaxants.

The authors are unaware of any information sources that describe the use of alternating current being passed through a muscle for the purposes of controlling biotechnical devices.

The method closest to the claimed invention is assumed to be the method of bionic control of technical device movements (WO #2012150500, 2012), which describes the generation of a control signal by means of recording the muscle electrophysiological signal, processing and forwarding the same to the control unit and subsequently to the executive mechanism.

Disadvantages of the method, similar to the earlier mentioned methods, consist in the fact that a control signal is generated on the basis of just bioelectrical activity of the muscles themselves arising as a result of movement intentions of the prosthesis user.

SUMMARY

The technical purpose of this invention is to provide an opportunity to obtain a high-quality and stable signal, allowing, in operating a technical device, to generate controlling actions proportional to the degree of muscular contraction with a delay of max, 120 ms.

The technical result in this case consists in the provision of an opportunity to obtain a control signal based on the recording of muscle contraction in time.

It has become possible in this case to track down, record and transform "the movement of the muscle itself" in time into a control signal, while the prior-art methods of recording muscle biopotentials with the help of myo-sensors record just the beginning of a contraction.

To achieve the technical result, the method of bionic control of technical devices comprising generation of a control action by means of recording an electrophysiological signal from the contracting muscle, processing and forwarding the same to the control unit and subsequently to the executive mechanism, further comprises the recording of the electrophysiological signal by passing alternating electric current through the muscle and determining electrical impedance, with the change of electrical impedance at muscle contraction being used as a control action.

Therefore, an electrical impedance signal is used as an electrophysiological signal.

Preferably, electric current with a frequency of from 10 kHz to 100 MHz and current amplitude of 0.01 to 10 mA is used.

Preferably, electric current is passed with the use of current electrodes placed on the skin surface or inside the tissues.

Preferably, the electrodes are placed on antagonistic muscles.

Preferably, the electrical impedance signal is recorded concurrently with the electromyogram signal of the contracting muscle.

Preferably, the electromyogram signal frequency range is from 50 to 400 Hz.

Preferably, both signals together are used as the control action.

Preferably, an impedance measuring transducer is used to record the electrical impedance signal and the electromyogram signal concurrently.

In a preferred embodiment, prostheses of the upper extremities are used as the technical device.

In another preferred embodiment, a computer is used as the technical device.

In another preferred embodiment, a game console is used as the technical device.

In another preferred embodiment, a robotic device is used as the technical device.

DETAILED DESCRIPTION

Figure 1:
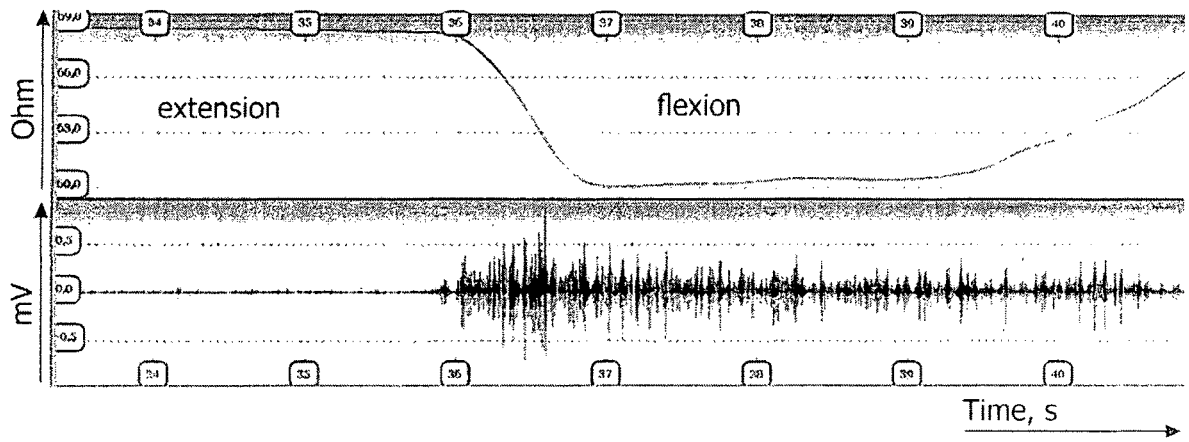
FIG. 1. Synchronous recording of electrophysiological signals including electrical impedance and electromyogram (EMG) signal.

FIG. 1 shows (as one embodiment) a synchronous recording of the electrophysiological signal being that of electrical impedance, and electromyogram signal (EMG), from electrodes placed on the skin surface over the finger flexor muscle during the performance of the hand grip movement.

Figure 2:
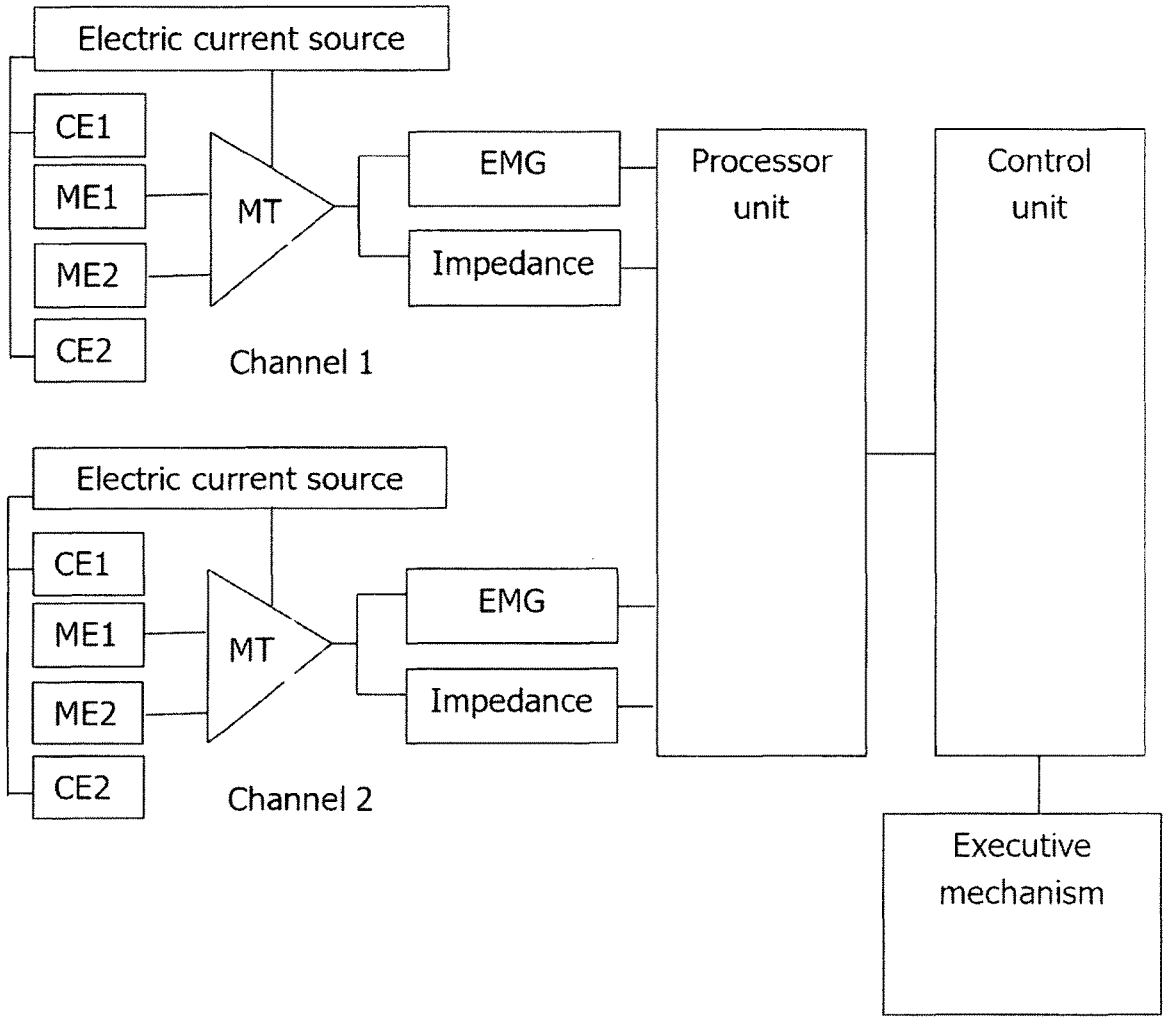
FIG. 2. Design of electrophysiology recording device.

To realize the method in practice, the authors have developed a device design shown in FIG. 2, where CE is a current electrode, ME is a measuring electrode, and MT is a measuring transducer.

Figure 3:
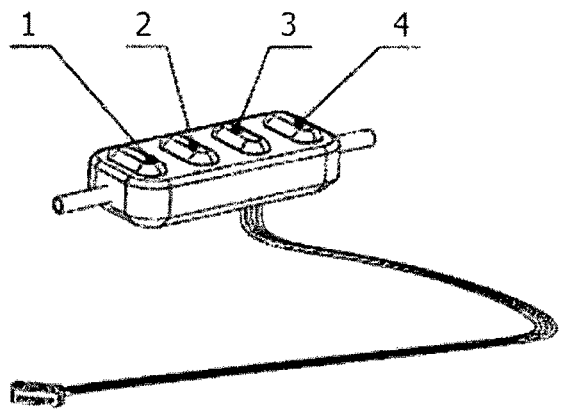
FIG. 3. Electrode system with foundation and electrodes.

The authors have also developed electrode systems consisting of a foundation (made of rubber or plastic) with four electrodes affixed thereto, as shown in FIG. 3.

Current is applied via electrodes 1 and 4 (current electrodes), and voltage is measured as a difference of potentials between electrodes 2 and 3 (potential electrodes).

Figure 4:
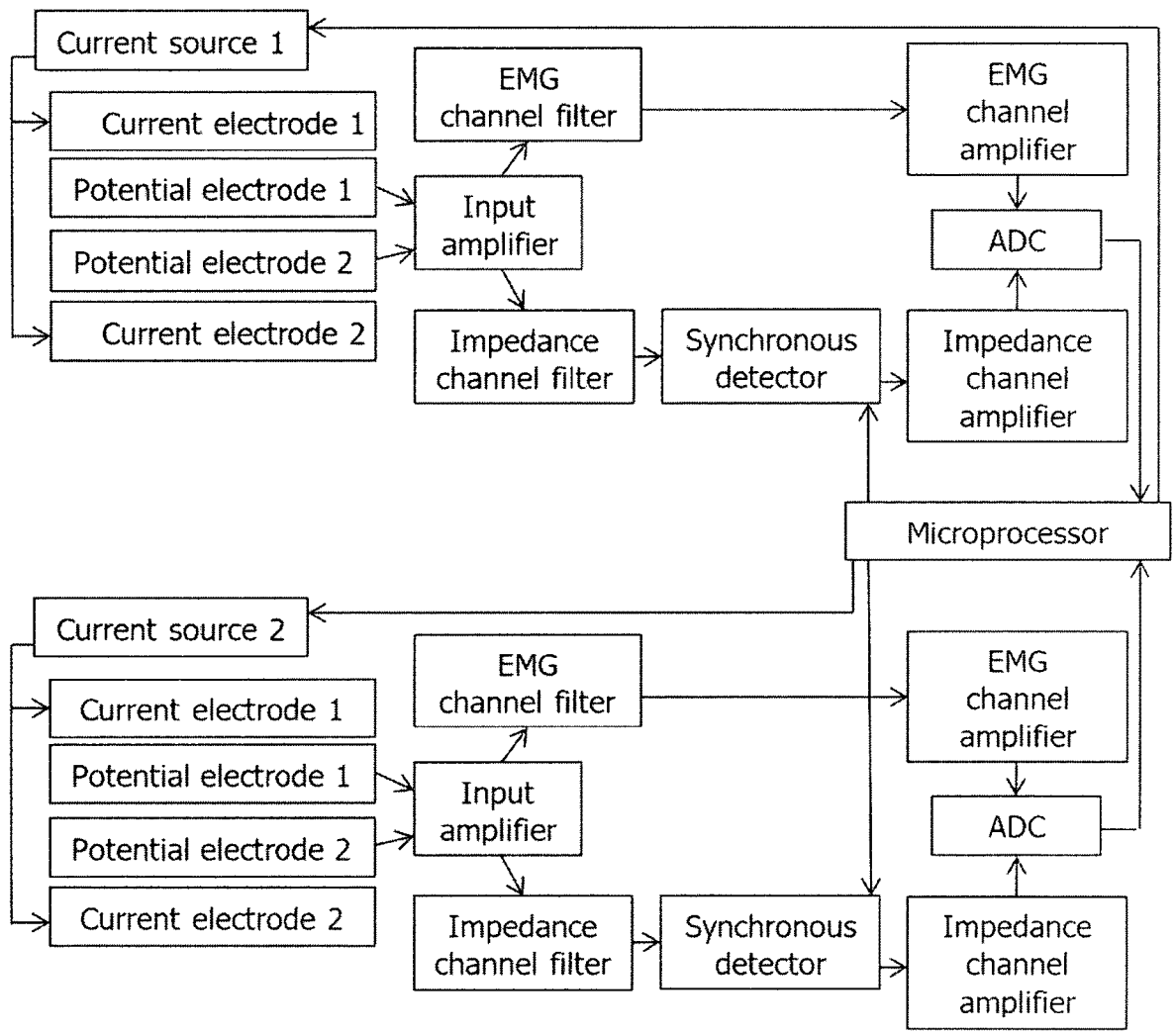
FIG. 4. Flow chart for recording an electrophysiological signal from contracting muscle.

The method is performed according to the chart shown in FIG. 4.

The microprocessor generates control signals to current source 1, which passes alternating electric current (frequency 100 kHz, amplitude 3 mA) through current electrodes placed on the skin surface over the muscle.

Voltage at potential electrodes recorded by the input amplifier is an algebraic sum of the common-mode interference, EMG signal and amplitude-modulated potential at the frequency of 100 kHz arising as a result of the difference of potentials from the action of the current source (the electrical impedance signal). The primary purpose of the input amplifier is common-mode interference suppression.

The EMG signal is separated from the electrical impedance signal by means of a bandwidth filter with a passband of from 50 Hz to 400 Hz (the EMG channel filter). The amplitude-modulated electrical impedance signal is separated from the EMG signal by means of a bandwidth filter with a passband of from 10 kHz to 1 MHz (the impedance channel filter) and is detected by a synchronous detector. For the synchronous detector operation, the microprocessor generates the same reference signal to function as a carrier reference frequency as for the respective current source. After further amplification, both channels are digitized by an analogue-digital converter (ADC). Thus, a control signal from one muscle is obtained.

However, to obtain a higher-quality and more stable technical device control signal, the second channel of the device should be used, which, operating in a similar way, records an electrical impedance signal and EMG signal from the second, antagonistic, muscle.

To exclude the reciprocal influence of the two electrical impedance channels, phase or time division of channels is used. In the case of phase division of channels, current source 1 generates a sine wave, and current source 2 a cosine wave. In the case of time division of channels, current sources operate in turn at different times.

Figure 5:
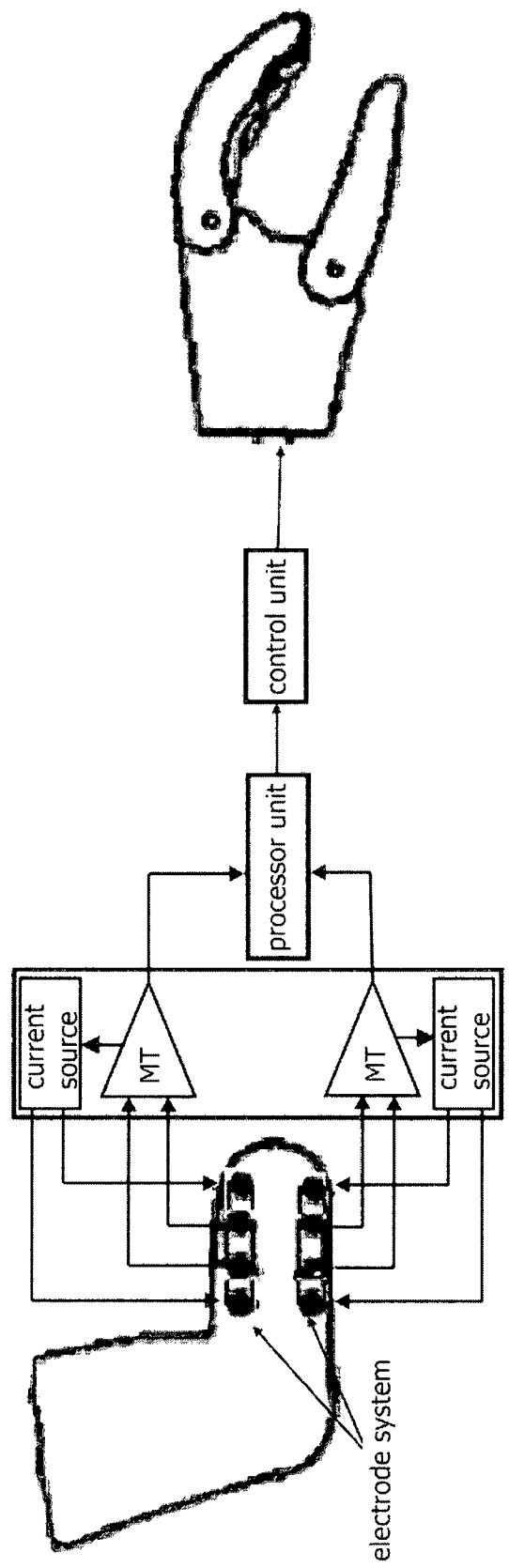
FIG. 5. Device for bionic control of a hand prostheses.

One of the possible options for using the proposed method may be a device for bionic control of a hand prostheses consisting of: two tetrapolar electrode systems; a two-channel impedance measuring transducer; a processor unit; a control unit; and an executive mechanism, namely a hand prostheses, as shown in FIG. 5.

Figure 6:
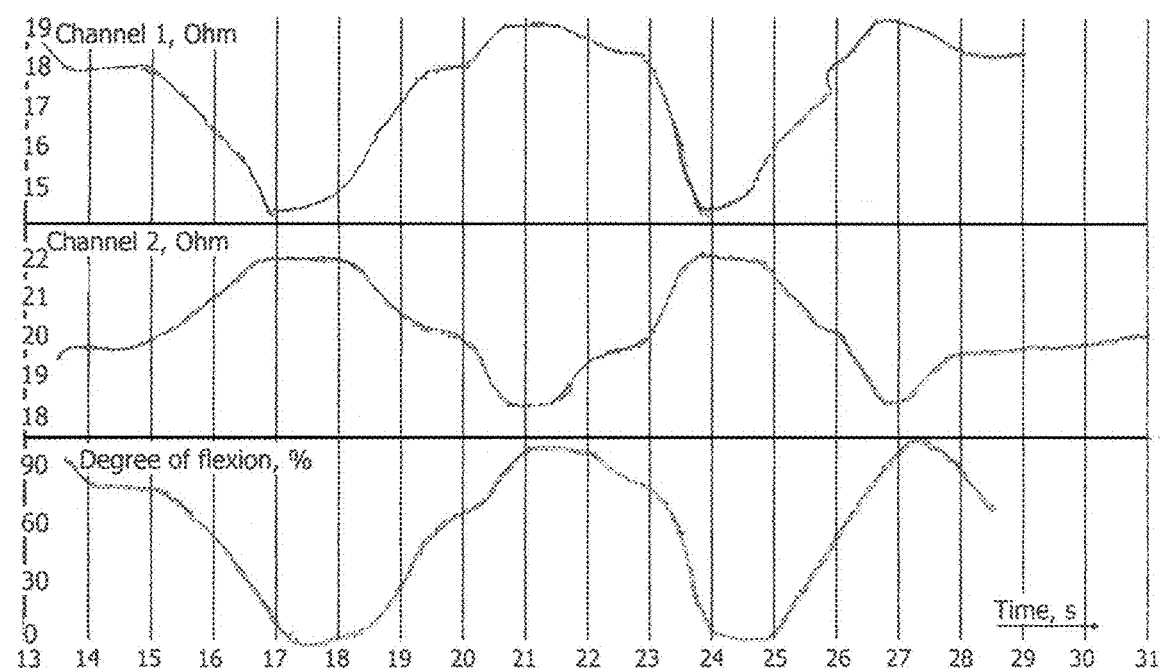
FIG. 6. Graphs showing tension and relaxation of muscles as in the natural movements of extending and flexing a wrist.

The electrode systems are positioned on the stump, in the projections of the remaining antagonistic muscles (wrist extensors and flexors). The amputee tenses and relaxes his muscles in the same manner as in the natural movements of extending and flexing the wrist (shown in FIG. 6.)

In the extension of the wrist (second 17), the impedance of the first measuring channel (the extensor channel) decreases, while the impedance of the second measuring channel (the flexor channel) increases. In the wrist flexing (second 21), the process is reverse.

In this example, the processor unit calculates the degree of wrist flexion (0% —the wrist is fully extended, 100% —the wrist is fully flexed) according to formula $$\frac{(I_1 - I_2) - \min(X_1 - X_2)}{\max(X_1 - X_2) - \min(X_1 - X_2)} * 100\%$$

where $I_1$, $I_2$ are the currently observed impedance values of the first and second channels, respectively;

$\min(X_1-X_2)$ is the minimum impedance difference value between the first and second channels; and $\max(X_1-X_2)$ is the maximum impedance difference value between the first and second channels.

In this example:

$\min(X_1-X_2)=14.5-22=-7.5$ (ohm)—is achieved at the point of time of 17 seconds, and $\max(X_1-X_2)=19-18.5=0.5$ (ohm)—is achieved at the point of time of 21 seconds.

Therefore, we can calculate the degree of wrist flexion at any point of time, for example, for the $20^{th}$ second:

$$\frac{(18-20)-(-7.5)}{0.5-(-7.5)} * 100\% = 69\%$$

The calculated values of the current degree of wrist flexion are transmitted to the control unit, which generates corresponding commands for the executive mechanism (the wrist) that are necessary to achieve the required degree of flexion.

The following examples are provided to illustrate the present invention without limiting the scope hereof.

Example 1. Controlling an Exoskeleton

The control and operation of an exoskeleton are performed similarly with a number of differences. The electrode systems are placed in the projections of antagonistic muscles. The operator performs natural movements with these muscles (for example, flexes and unflexes the wrist). The degree of wrist flexion having been calculated, the signal is transmitted to the control unit and further to the executive mechanism (the exoskeleton drive). To control different movement types, it is necessary to place two pairs of electrode systems on each respective antagonistic muscle.

Example 2. Controlling a Computer (for Example, Sound Volume)

Electrode systems are placed in the projections of antagonistic muscles (for example, wrist flexors and extensors) on the healthy hand or on the stump (if the operator is an amputee). The calculated currently observed degree of wrist flexion is transmitted to the control unit, which connects with the computer via one of the standard interfaces (USB, serial port, infrared port). The special computer software receives the transmitted information on the degree of wrist flexion and sets the sound volume corresponding to the current degree of wrist flexion.

What is claimed is:

1. A method of enhancing mechanical function in a subject with a prosthetic device, the method comprising:
   using electrodes to pass an alternating current through a muscle in the subject to cause the muscle to contract,
   using a first recording electrode to record an electrical impedance signal from the contracting muscle,
   using a processor to generate a control signal that is based on a change in the electrical impedance in the muscle in real time during contraction of the muscle,
   forwarding the control signal to a controller, and
   controlling the prosthetic device with the controller and control signal to achieve the enhancement of mechanical function in the subject, the enhancement of mechanical function occurring by mechanical function of the prosthetic device.

2. The method of claim 1, wherein the alternating current has a frequency of from 10 kHz to 100 MHz and an amplitude of from 0.01 to 10 mA.

3. The method of claim 1, wherein the alternating current is passed through the muscle and wherein the electrodes used to pass the alternating current through the muscle are placed on a skin surface or inside a tissue adjacent to the muscle.

4. The method of claim 1, wherein the muscle is antagonistic to another muscle.

5. The method of claim 1, further comprising using second recording electrode to record an electrophysiological signal, which is an electromyogram signal of the contracting muscle, wherein the electrical impedance signal and the electrophysiological signals are recorded concurrently.

6. The method of claim 5, wherein the electromyogram signal is recorded at a frequency range of from 50 to 400 Hz.

7. The method of claim 1, wherein both the change in electrical impedance and an electromyogram signal from the muscle in the subject together are used as the control signal.

8. The method of claim 1, wherein the prosthetic device is configured to be used in association with an upper extremity of the subject.

9. A method of enhancing mechanical function in a subject with a prosthetic device, the method comprising:
    using electrodes to pass an alternating current through a muscle in the subject to cause the muscle to contract,
    using a first recording electrode to record a first electrophysiological signal from the contracting muscle,
    processing the first electrophysiological signal with a processor to determine a measurement of electrical impedance in the muscle,
    using the processor to generate a control signal that is based on a change in the electrical impedance in the muscle in real time during contraction of the muscle,
    forwarding the control signal to a controller, and
    controlling the prosthetic device with the controller and control signal to achieve the enhancement of mechanical function in the subject, the enhancement of mechanical function occurring by mechanical function of the prosthetic device.

10. The method of claim 9, wherein the alternating current has a frequency of from 10 kHz to 100 MHz and an amplitude of from 0.01 to 10 mA.

11. The method of claim 9, wherein the alternating current is passed through the muscle and wherein the electrodes used to pass the alternating current through the muscle are placed on a skin surface or inside a tissue adjacent to the muscle.

12. The method of claim 9, wherein the muscle is antagonistic to another muscle.

13. The method of claim 9, further comprising using a second recording electrode to record a second electrophysiological signal, which is an electromyogram signal of the contracting muscle, wherein the first and second electrophysiological signals are recorded concurrently.

14. The method of claim 13, wherein the electromyogram signal is recorded at a frequency range of from 50 to 400 Hz.

15. The method of claim 9, wherein both the change in electrical impedance and an electromyogram signal from the muscle in the subject together are used as the control signal.

16. The method of claim 9, wherein the electrical impedance and the electromyogram signal from the muscle in the subject are concurrently recorded.

17. The method of claim 9, wherein the prosthetic device is configured to be used in association with an upper extremity of the subject.

* * * * *